(12) United States Patent
Brady et al.

(10) Patent No.: US 12,005,077 B1
(45) Date of Patent: Jun. 11, 2024

(54) BROAD-SPECTRUM ANTIMICROBIAL, BIOCOMPATIBLE AND PRESERVATIVE-FREE FUNCTIONALIZED FULLERENES OPHTHALMIC SOLUTION WITH REACTIVE OXYGEN SPECIES SCAVENGING AND ADVANCED TARGETING, PENETRATION, AND HYDRATION

(71) Applicants: Terry Earl Brady, The Valley (AI); Anthony Lee Dellinger, Burlington, NC (US); Lowell Hughes, The Valley (AI); Melinda K. M. Goddard, The Valley (AI); Christopher E. Starr, New York, NY (US); Abed Alqader Ibrahim, Greensboro, NC (US)

(72) Inventors: Terry Earl Brady, The Valley (AI); Anthony Lee Dellinger, Burlington, NC (US); Lowell Hughes, The Valley (AI); Melinda K. M. Goddard, The Valley (AI); Christopher E. Starr, New York, NY (US); Abed Alqader Ibrahim, Greensboro, NC (US)

( * ) Notice: Subject to any disclaimer, the term of this patent is extended or adjusted under 35 U.S.C. 154(b) by 0 days.

(21) Appl. No.: 18/374,342

(22) Filed: Sep. 28, 2023

(51) Int. Cl.
*A61K 33/44* (2006.01)
*A61K 33/38* (2006.01)
*A61K 45/06* (2006.01)
*A61K 47/36* (2006.01)

(52) U.S. Cl.
CPC .............. *A61K 33/44* (2013.01); *A61K 33/38* (2013.01); *A61K 45/06* (2013.01); *A61K 47/36* (2013.01)

(58) Field of Classification Search
CPC ........ A61K 33/44; A61K 33/38; A61K 45/06; A61K 47/36
See application file for complete search history.

(56) References Cited

U.S. PATENT DOCUMENTS

| | | | |
|---|---|---|---|
| 10,934,168 B1 * | 3/2021 | Brady | D06M 16/00 |
| 2009/0163447 A1 * | 6/2009 | Maggio | A61K 9/0048 514/415 |
| 2015/0250891 A1 * | 9/2015 | Venkatraman | A61K 9/0019 514/274 |

OTHER PUBLICATIONS

Biswas, Kunal et al. "Exploring the Bioactive Potentials of C60-AgNPs Nano-Composites against Malignancies and Microbial Infections." International Journal of Molecular Sciences. 2022; 23(2):714. https://doi.org/10.3390/ijms23020714. (Year: 2022).*

* cited by examiner

*Primary Examiner* — Frederick F Krass
*Assistant Examiner* — Lucy M Tien (57) ABSTRACT

The present invention introduces an ophthalmic solution containing halo-fullerenes. When the spherical fullerene carbon cages are functionalized with halogens, the resulting halo-fullerenes demonstrate sustained antimicrobial activity. Fullerenes are also characterized by unique electron properties that impart antioxidant capabilities as free radical scavengers. Nonetheless, far smaller than ocular tissue cells, halo-fullerenes are biocompatible—and capable of penetrating intricate barriers, like the cornea and conjunctiva, with potential to achieve greater efficacy and symptom relief in chronic dry eye than conventional treatments. With remarkable surface area, halo-fullerenes also allow customization and possess a unique molecular architecture for broader applications. This multifunctional solution thus imparts antimicrobial activity, antioxidative protection, molecular lubrication, and shielding from external irritants while penetrating dense ocular structures. Without the need for antibiotic additives or preservatives, the invention can offer an effective, safe option for dry eye treatment, prophylaxis in contact lens solutions, and post-surgical care.

18 Claims, 6 Drawing Sheets

BROAD-SPECTRUM ANTIMICROBIAL, BIOCOMPATIBLE AND PRESERVATIVE-FREE FUNCTIONALIZED FULLERENES OPHTHALMIC SOLUTION WITH REACTIVE OXYGEN SPECIES SCAVENGING AND ADVANCED TARGETING, PENETRATION, AND HYDRATION

FIELD OF THE INVENTION

This innovation pertains to a novel ophthalmic solution composition that incorporates functionalized halo-fullerenes to address the persistent challenge of optimizing drug delivery, specifically in the context of chronic dry eye in the first instance and as a prophylactic component in contact lens cleaning, wetting, and storage solutions. Halo-fullerenes possess broad-spectrum antimicrobial activity and unmatched antioxidant properties, foster a healthier ocular environment by stimulating cellular growth, provide molecular lubrication, and mitigate oxidative stress. This innovation provides a multifaceted approach, combining surface and interstitial antimicrobial activity, resulting in a comprehensive ophthalmic solution. The composition obviates the necessity for potentially harmful additives like antibiotics, antifungals, and preservatives, ensuring biocompatibility. The invention provides a comprehensive solution to enhance cellular vitality and overall well-being through the application of nanoparticle technology.

BACKGROUND OF THE INVENTION

Each human eye is located in an orbit, of which it occupies roughly one-fifth of the total space. The extraocular muscles, fatty tissues, nerves, blood vessels, fascia, and the lacrimal gland occupy the remaining portion of the region. Eyes can be affected by amblyopia, color blindness, floaters, dry eye, and many other diseases. Chronic dry eye (CDE), also known as dry eye syndrome (DES) or dry eye disease (DED), is also a common ailment.

The layers that comprise normal tear film must all function properly and maintaining homeostasis for comfort and, more importantly, for clear vision. The essential, watery tear layer is protected by an outer layer of Meibomian gland oily secretions and the innermost layer on the cornea, which comprises a thin lipid layer and an inner mucoaqueous layer and allows the watery tear component to moisten the cornea. Blinking serves to continuously maintain and replenish this film. CDE is characterized by a loss of lubrication and moisture homeostasis on the eye's surface that is perpetuated by a vicious cycle of tear hyperosmolarity, tear instability and inflammation, leading to ocular surface damage.

The ocular region is an intricate tapestry of densely packed cells, especially in areas such as the cornea and retina. This region exhibits a sophisticated cellular complexity and structural intricacy, exemplified by specialized cells densely arrayed, particularly within the cornea and retina. These formations are pivotal for ocular health, influencing conditions like CDE. The density and tight junctions between these cells have evolved to serve multiple purposes, from protecting the inner eye from potential pathogens, to maintaining the precise ocular refractive properties necessary for clear vision. The cornea, a transparent structure at the eye's forefront, owes its clarity to its unique cellular composition and layout. The outermost layer of the region, corneal epithelium, contains tightly packed, stratified squamous epithelial cells that act as an environmental barrier. In contrast, the innermost, the endothelium region, comprises a solitary layer of hexagonal cells that ensure the cornea's dehydration and, by extension, its transparency. Furthermore, the light sensitive retinal layer at rear of the eye contains photoreceptor cells (i.e., rods and cones). These cells, densely packed especially in the fovea, capture light and transform it into neural signals. While these cellular arrangements are vital for ocular function, they pose significant obstacles to the delivery and permeation of therapeutics.

The cornea and conjunctiva are the main tissue barriers that prevent drugs from being absorbed into the eye after administration. As such a barrier and yet a pathway for drug absorption into the eye's aqueous humor, the cornea serves as the most often employed site in examination of ocular bioavailability. The conjunctival epithelium possesses intercellular tight junctions, but it is more porous than the cornea, with 17 times greater surface area. Ocular absorption of drugs can occur through the conjunctiva, especially to the iris and ciliary body, however, trans-conjunctival permeation can also result in systemic drug absorption from the conjunctival sac.

The corneal exterior, as the foremost boundary, presents substantial resistance to topically applied therapeutics. Compact, hydrophobic epithelial cells limit the diffusion of hydrophilic agents, while the hydrophilic nature of the corneal stroma hampers the penetration of hydrophobic compounds. The ocular penetration of topically administered therapeutics is thus hindered, with 5% of a typical dose reaching the intraocular domain. Most ophthalmic solutions are eliminated through tear secretion, metabolic processes, or retention within the corneal epithelial layer. The inherent barriers designed by the ocular anatomy complicate their delivery to interior regions like the retina. Though systemic and oral pathways are alternatives, they often necessitate augmented doses, posing risks of systemic adverse reactions. Any perturbation in the specialized cells in this region can likewise culminate in ocular ailments such as CDE. The design that is integral to vision thus imposes hurdles for therapeutic interventions, necessitating continual innovation to ensure efficacious ocular treatments.

The health of the ocular surface relies heavily on the Meibomian glands, situated within the eyelids. These glands lubricate the eye through the production of the oily lipid layer of the tear film, which is essential for preventing rapid tear evaporation and maintaining optimal ocular lubrication. A leading diagnosis underlying CDE is associated with Meibomian Gland Dysfunction (MGD), whereby the narrow glandular passages become blocked and inhibit proper lubrication. This causes the aqueous layer of the tear film to evaporate faster, resulting in dry, irritated eyes. However, current methods for clearing blocked passages do not consistently provide relief for all patients.

In fact, a specific cause for CDE remains uncertain, and the condition may be the result of an array of maladies. Notably, CDE manifestations vary from patient to patient and from day to day, by individual, suggesting changes in interstitial and cell surface moisture. Beyond the effects associated with Meibomian dysfunction, other conditions can exacerbate CDE, including use of contact lenses. For example, the deleterious effects of free radicals have been implicated as a factor during the early stages of some ocular diseases. Free radicals can be attributed to intrinsic factors, like metabolic activities, as well as extrinsic factors such as radiation, medication, and environmental pollutants. These highly reactive molecules, bearing an unpaired electron in their outermost shell, initiate a milieu of cellular chain reactions that degrade critical organic molecules like DNA, proteins, and lipids. The accumulation or overabundance of free radicals leads to oxidative stress in the tissue microenvironment which can advance ocular ailments, including cataracts, glaucoma, and diabetic retinopathy.

In addition, the eyes are regularly exposed to light and oxygen, making them vulnerable to oxidative damage. Over time, this can damage ocular cells, especially photoreceptor cells in the retina, leading to conditions like age-related macular degeneration. Notably, the onslaught of free radicals and oxidative stress results in chronic inflammation and cell death. In conditions like CDE, this chronic inflammation can also stimulate the immune system to attack the lacrimal or Meibomian gland and further impact both tear production and quality.

Antioxidants function as our primary defense against the effects of free radicals. By curtailing free radical production, neutralizing existing radicals, and ameliorating the consequent cellular damage, they mitigate oxidative stress. Emerging research indicates that antioxidants could modulate immune responses, a potential benefit for inflammation-driven conditions like dry eye syndrome. Yet, efficient antioxidant delivery, especially to the eye, remains a challenge.

Although the symptoms of dryness, scratchiness, and burning can be temporarily relieved, dry eye is a persistent disease for which no cure has been found. Symptoms are typically soothed with artificial tears, which mimic the natural tear composition and lubricate the eye. However, a myriad of prescription and over the counter (OTC) formulations can be confusing to sufferers while providing varying levels of relief for some patients but not others. It is also challenging to measure corneal moisture absorption of such therapeutics directly, which leads to reliance on empirical symptom relief and external examinations.

The medical administration of ocular drops has played an integral role in managing various eye conditions, albeit with reported complications attributed to their formulations. Specifically, the preservatives in some ophthalmic medications have also been presumed to exacerbate CDE, adding to the complexities associated with this condition—and spawning preservative-free alternatives, including single-dose applications with more packaging than medication.

Such compounds, like benzalkonium chloride (a common preservative), can be particularly harsh, causing irritation, redness, and even worsening dry eye symptoms (exacerbating epithelial toxicity) (Starr et al., 2019). In addition to preservatives, viscosity-enhancing agents designed to prolong retention on the eye can also inadvertently reduce natural tear drainage and obstruct the Meibomian glands.

Ophthalmic antibiotics, commonly used in eye drops, such as ciprofloxacin, ofloxacin, and moxifloxacin, while effective, have likewise been associated with drawbacks and long-term side effects. For instance, at relatively low concentrations (0.3% to 0.5%), these antibiotics can rapidly penetrate the cornea and aqueous humor with unintended cytotoxicity, irritation, and allergic reactions. (Silva et al., 2017). Although the incorporation of antibiotics in ocular drops enhances their practicality (e.g., in multi-use dropper bottles) and extends shelf-life while mitigating microbial contamination, their potentially deleterious effects cannot be overlooked. Vaede (et al. 2010) and Baudouin (et al. 2010) emphasized these risks, which can vary depending on concentration and exposure duration, as validated by Fernández-Ferreiro (et al. 2016). Given that many therapeutic compositions therefore threaten the structural and functional integrity of sensitive ocular tissues, there is a pressing need for innovation, especially regarding alternatives to the use of such additives.

As noted, various factors contribute to CDE; however, its increasing prevalence has been associated with aging populations, hormonal changes, inflammation, the patient's environment, increases in contact lens use, and allergies. Notably, the characteristic, diminished frequency of blinking during digital screen use and increased use of face masks led to more cases of CDE during the COVID-19 pandemic. One study conducted at the University of West Indies revealed a sharp rise in symptomatic CDE from 48.1% prior to the COVID-19 pandemic to 62.4% during lockdowns (Ezinne et al., 2023).

CDE and other ocular conditions significantly impact millions worldwide, leading to visual impairment and constant discomfort for those affected. CDE cases are diverse and can lead to substantial treatment expenses. If untreated, CDE can escalate to cause severe inflammation and corneal abrasions affecting epithelial cells.

In 2017, based on weighted statistics, more than 16 million individuals in the United States were deemed to have been diagnosed with CDE (Farrand et al., 2017), but the actual count, including those undiagnosed, is presumably much greater. Using a simple TBUT (tear break up time) test, as many as 54.8% of 400 patients over the age of 40 were diagnosed with CDE in one study (Shah and Jani, 2015). The CDE annual financial toll in the US was estimated to be $60 billion as early as 2007 (Miljanović et al., 2007). Given the scale of this confounding and chronic condition, many researchers have shared and patented innovations emerging from their work in pursuit of addressing CDE.

Chinese Patent CN104644550A, Curcumin nano micelle eye drops as well as preparation method and application, discloses an eye drops composition with nano-micelles of curcumin. The eye drops comprise 0.005-0.02% curcuminoid, a 0.01-0.1% (by mass volume) nano-micelle drug delivery system made of chitosan, alongside a surfactant, co-surfactant and pharmaceutical-grade water. The curcumin-containing nano-micelle eye drop formulation is stable, with enhanced bioavailability for reduced dosage. The formulation described in CN104644550A focuses on curcumin nano-micelle eye drops. It does not teach the use of functionalized fullerenes and composite nanoparticles that provide broad-spectrum antimicrobial activity, antioxidant capabilities, increased wettability, molecular lubrication, and hydration to enable delivery penetration to treat or prevent ocular conditions, especially CDE.

In patent CN113520997, Natamycin and silver loaded nano mesoporous carbon eye drops and preparation method and application thereof, the disclosed art pertains to an eye drop formulation comprising natamycin and silver incorporated into nano mesoporous carbon, alongside methods for its synthesis and application. The formulation entails the integration of silver and natamycin onto the nano mesoporous carbon, as a base for the solution. This nano mesoporous carbon enables drug-loading capabilities and provides an expansive surface area to facilitate the sustained release of natamycin, for solubility and bioavailability. The nano mesoporous carbon can also bind inflammatory factors, providing inflammation mitigation. The embedded silver in the mesoporous carbon structure extends antifungal duration, lessening the natamycin dose and minimizing potential side effects. The art described in CN113520997 in turn centers on the use of natamycin and silver within nano mesoporous carbon for addressing fungal keratitis; whereas the proposed patent does not comprise antifungal constituents. CN113520997 also does not teach a functionalized fullerene and composite nanoparticle engineered to increase delivery penetration for use as ocular treatments or preventives for broad-spectrum antimicrobial and antioxidant applications, with enhanced wettability, molecular lubrication, and hydration.

The patent CN114129515B, Tofacitinib nano crystal eye drop and preparation method thereof, discloses a formulation comprising tofacitinib nano-crystal eye drops designed for the treatment of immune-related ocular conditions and a method for preparation. The disclosed composition includes a surfactant, P188-lecithin, and a stabilizer (HPMC, polyvinyl alcohol, or HPMC-docusate sodium, or a combination thereof). The invention teaches a synergy between the surfactant and stabilizer that aids in modulating the particle size and potential of the eye drops. This synergy also enhances the stability, stickiness, and longevity of the medication within the eye, leading to a higher drug delivery, minimizing medication loss prior to reaching the cornea, and ensuring prolonged drug release. Together, the composition enables a reduced frequency of application that elevates patient compliance for clinical applications. The proposed patent differs from CN114129515B in both active ingredients and formulation, notably the inclusion of functionalized fullerenes and nanoparticles and the absence of immunosuppressing compounds (Tofacitinib). These additives have been shown to cause local irritation, increase the risk of infection and alter ocular surfaces to impact tear production or cause long-term adverse effects.

Chinese Patent CN114712389A, Nano cerium dioxide eye drops and preparation method and application thereof, describes an eye drop containing nano cerium dioxide and the method of formulation. The patent teaches the properties of nano cerium dioxide, which has numerous surface imperfections with active oxygen binding sites that enhance antioxidant potential and counteract oxidative stress-induced damage due to high glucose levels. The described composition claims superior permeability of nano cerium dioxide to ocular tissues. It also presents a non-invasive, peripheral eye treatment for cataracts that combines cost-efficiency and safety. The proposed patent diverges from CN114712389A by using functionalized fullerenes and composite nanoparticles that confer broad-spectrum antimicrobial and antioxidant activity, as well as enhanced wettability, molecular lubrication, hydration, and delivery penetration, particularly targeting treatment and prevention of conditions like CDE. Furthermore, the art of the proposed patent diversifies the therapeutic spectrum, providing multifaceted benefits beyond the scope of CN114712389A.

In patent KR101492447B1, Eye composition containing a cyclosporine and a method of preparing the same, the disclosure pertains to a nano-emulsion, topical formulation designed to enhance the solubility of cyclosporin. This formulation is achieved by combining cyclosporin, a non-aqueous solvent, an emulsifier, and an aqueous solvent, along with a method for its production. The characterized nano-emulsion has an average particle size of 200 nm or less, optimally around 100 nm or less, with a limited particle disparity. The topical formulation is described as an ocular solution designed to reduce foreign-body sensations and enhance visual clarity. The art described in KR101492447B1 does not teach the use of functionalized fullerenes or nanoparticles with broad-spectrum antimicrobial activity and antioxidant capacities that increase ocular wettability, molecular lubrication, and hydration.

Chinese patent CN102210849A, Preparation of cyclosporine A nano-particle eye drop, discloses an eye drop formulation comprising a cyclosporine A-loaded polyethylene glycol-polylactic acid copolymer, nanoparticle solution. The art teaches a nano eye drop synthesized using two methods. First, dissolve the polymer and cyclosporine A in an organic solvent with a surfactant, followed by high-pressure homogenization to form an emulsion. The organic solvent is removed using a rotary evaporator, and the residue is re-dissolved in normal saline to yield the desired nano eye drop. The second method entails dissolving the polymer and cyclosporine A in an organic solvent, which is then added incrementally into water under magnetic stirring. These formulations are described to enhance the water solubility of cyclosporine A. The art described in CN102210849A does not teach the use of fullerenes, functional fullerenes and nanoparticles for ocular formulations with broad-spectrum antimicrobial activity and antioxidant capacities and molecular lubrication that increase ocular wettability and hydration.

In patent CN107115299B, Rapamycin nano micelle eye drops and preparation method thereof, a method is described for preparing rapamycin nano-micelle eye drops. The process involves combining a polyvinyl caprolactam-polyvinyl acetate-polyethylene glycol graft copolymer with rapamycin, absolute ethyl alcohol, and glucose to produce a rapamycin-containing mixture. The mixed solution is evaporated, hydrated, and chilled for clarification, resulting in a rapamycin nano-micelle eye drop. The eye drops extend the lifespan of corneal implants, mitigate inflammatory cell invasion, curb corneal swelling, and preserve the natural structure of the corneal graft. The art described in CN107115299B nonetheless fails to teach the use of fullerenes, functional fullerenes and nanoparticles for ocular formulations with broad-spectrum antimicrobial and antioxidant activity and molecular lubrication that increase ocular wettability and hydration.

In patent CN100444897C, Nano complex eye drops containing liposoluble compound drug and its preparing method, a nano-complex eye drop formulation of liposoluble compound drugs is described, along with a method of preparation. The components of the nano-complex eye drop include calcium phosphate nanoparticles, medlar-derived (Chinese medicinal) active substances, liposoluble compound drugs, distilled water, an osmoregulation agent, and a preservative. The nano-complex eye drop describes: an enhanced diffusion rate of liposoluble compound drugs in aqueous solutions, facilitation of drug delivery through the cornea to elevate drug concentration in the aqueous humor, prolongation of the drug therapeutic concentration after administration, biological efficiency, and absence of adverse effects. The art described in CN107115299B, however, does not teach the use of fullerenes, functional fullerenes and nanoparticles for ocular formulations with broad-spectrum antimicrobial and antioxidant activity and molecular lubrication that increase ocular wettability and hydration. Furthermore, the proposed patent does not include the use of preservatives, in contrast to CN107115299B.

While the use of nanotechnology has shown promise for ophthalmological uses, there are no previous compositions that utilize engineered and functionalized halo-fullerenes. In fact, fullerenes are spherical, novel allotropes of carbon with unique electronic properties, high antioxidant capacities and biocompatibility suitable for medical applications. Their size, and ability to functionalize and modify fullerenes to alter specific surface properties, enables them to penetrate and reach specific targets within the eye for enhanced efficacy with fewer side effects.

The distinctive structure of the halo-fullerene also provides the particle with significant durability and incompressibility. The outer shell of the carbon cage acts as an electron reservoir, storing and releasing electrons as necessary. As such, halo-fullerenes can provide sustained free radical scavenging and neutralization of reactive oxygen species (ROS) to reduce oxidative stress. Their antimicrobial properties can likewise offer alternatives to traditional antibiotic additives.

While halo-fullerenes demonstrate remarkable endurance, the ocular region presents a distinct environment compared to the dynamic and continuously renewing skin. In the ocular region, key anatomy focus is directed at maintaining the well-being of ocular cells, where cellular turnover is comparatively slower and less characterized by the dynamic shedding of mature cells. Within the ocular region, the cellular composition includes specialized cell types such as corneal and conjunctival epithelial cells. These cells play a vital role in maintaining ocular health by forming protective barriers and ensuring the integrity of the eye's surface.

SUMMARY OF THE INVENTION

The proposed patent describes leveraging halogenated fullerenes in an ophthalmic suspension, particularly for the prevention and treatment of CDE and related symptoms. The invention teaches a multifunctional solution that is safe for ocular tissues and provides antimicrobial and antioxidant capabilities, molecular lubrication, and protection from environmental elements. The composition would have utility as a prophylactic for CDE and as a therapeutic for existing conditions, especially for contact lens use and post-surgical care (e.g., inadequate moisture, inflammation from pathogenic matter, and broad-spectrum oxidative stress).

In the primary embodiment, specially engineered halo-fullerenes (and/or an alternative nanomaterial-based composition) apply atomic scale properties to circumvent penetration challenges and allow for efficient navigation through dense ocular cellular configurations. Their quantum scale and unique properties thus facilitate therapeutic delivery with enhanced bioavailability and targeted ocular tissue distribution for treatments of numerous eye conditions. The formulation is biocompatible, effective, and free of traditional additives with consequent adverse effects.

In the present invention, the dispersion of halo-fullerenes in the suspension disrupts the hydrogen-bonding network of water molecules at the surface, leading to a decrease in surface tension. Lowering the surface tension of the aqueous solution enhances the ability to spread, penetrate and wet the applied surface area, imparting a surfactant-like effect. Furthermore, the halo-fullerenes enable the liquid delivery vehicle to interact with the ocular surface by enhancing the adhesion characteristics of the solution. By modifying the physical and chemical properties of the aqueous delivery suspension, altering the hydrogen-bonding networks of water, and imparting affinity between the liquid and surface area, halo-fullerenes allow for greater uptake within ocular tissues, including sensitive layers such as the cornea and conjunctiva. With this distinctive attribute, halo-fullerenes can be functionalized for precise targeting to pivotal regions within the eye for optimal therapeutic efficacy.

In the primary embodiment, the functionalized halo-fullerenes also provide potent antibacterial and antioxidant activity that protects ocular cells from microbes and free radicals. In addition to its ability to damage bacteria, halo-fullerenes can serve as an efficient free radical scavenging solution to offset effects of reactive oxygen species (ROS). These ROS are commonly connected to the oxidative stress that is a major cause of cellular deterioration, premature aging, and numerous ocular disorders. The ocular cells are notably subject to a slower turnover process, characterized by gradually replacing aging cells with newer ones. Once administered, halo-fullerenes could thus contribute to sustained ocular health, given the natural cellular processes of the eye.

These mechanisms of action offer more layers of defense since they are close to the ocular surface and throughout the cellular flattening process. The resulting effect is the maintenance of optimal moisture levels to prolong the vitality of ocular cells throughout their life cycle. This comprehensive strategy provides enhanced molecular lubrication, environmental protection and a more colorful visual experience.

The present invention also pertains to a formulated ophthalmic solution composition that encompasses halo-fullerenes enriched with silver nanoparticles, thiolated hyaluronic acid functionalized endohedral halo-fullerenes, hyaluronic acid-modified liposomal encapsulated functionalized endohedral halo-fullerenes, or combinations thereof. This nano-formulation can enhance ease of use and efficacy to address both immediate symptoms and causes, while suggesting longer term benefits from antioxidant and anti-inflammatory activity with continued use for CDE treatment as well as prevention in contact lens cleaning, wetting and storage solutions.

The ophthalmic suspension comprising halogenated fullerenes is inherently pathogen-free, ensuring an extended shelf life, with self-sterilizing properties to prevent atmospheric or contact contamination, without caustic additives or bactericides. This eliminates the contact contamination risks associated with multiuse dropper bottles. Likewise, whether multi-use or individual ampules, contamination cases have been traced back to manufacturing rather than end-users. Notably, conventional FDA-approved sterility testing focuses on detecting the presence of Lipopolysaccharides (LPS), often overlooking the potential presence of bacteria or fungi that could potentially proliferate within the liquid suspension over time. As such, Bacteria Endotoxin Testing (BET) required by the FDA is a method that specifically cannot detect gram-positive bacteria or fungi and is not a claim of sterility. Notably, 50% of pathogenic sepsis cases are caused by gram-positive bacteria or fungi in the hospital setting.

DETAILED DESCRIPTION OF THE INVENTION

The primary embodiment of the present invention thus comprises halo-fullerenes, endohedral halo-fullerenes and optionally functional AgNPs, hyaluronic acid (HA), and liposomes that are capable of moisture penetration of the ocular cell environment and layers of the cornea and conjunctiva, the primary tissues that otherwise limit the bioavailability of drugs following eye drop administration. The nano-formulation also minimizes systemic drug absorption from the conjunctival sac by focusing on drug delivery to target tissues within the eye, such as the iris and ciliary body.

Figure 1:
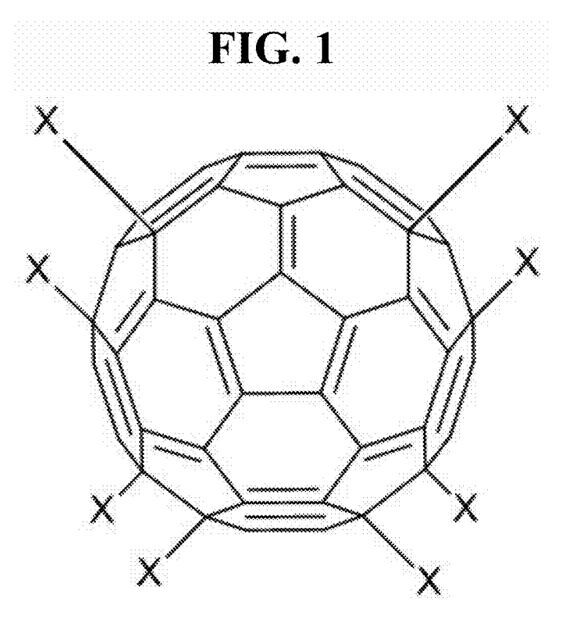
FIG. 1 is a molecular representation of an exemplary functionalized halo-fullerene of 60 carbons functionalized with halogens (X).

The primary embodiment of the ophthalmic solution composition of the present invention thus comprises: halo-fullerenes, a delivery vehicle, a penetration enhancer, optionally a pharmacologically active ingredient, and water. Wherein the halo-fullerene represents a fullerene of $C_{2n}$, whereby n=10, 12, 13, 14, 15, ..., 360 contains multiple side-chains halogens attached to the carbon cage. As shown in FIG. 1, an exemplary molecule of the present invention relates to $C_{60}$ fullerene functionalized with eight halogen molecules. In alternative embodiments, the halo-fullerene may comprise the three typical functionalization patterns including: $C_{60}X_6$, $C_{60}X_8$ (FIG. 1), and $C_{60}X_{24}$; whereby X=a halogen molecule (i.e., iodine, bromine, chlorine, and fluorine), preferentially chlorine. This imparts molecular affinity for pathogenic species to the halo-fullerenes for sustained microbial neutralization.

Figure 2:
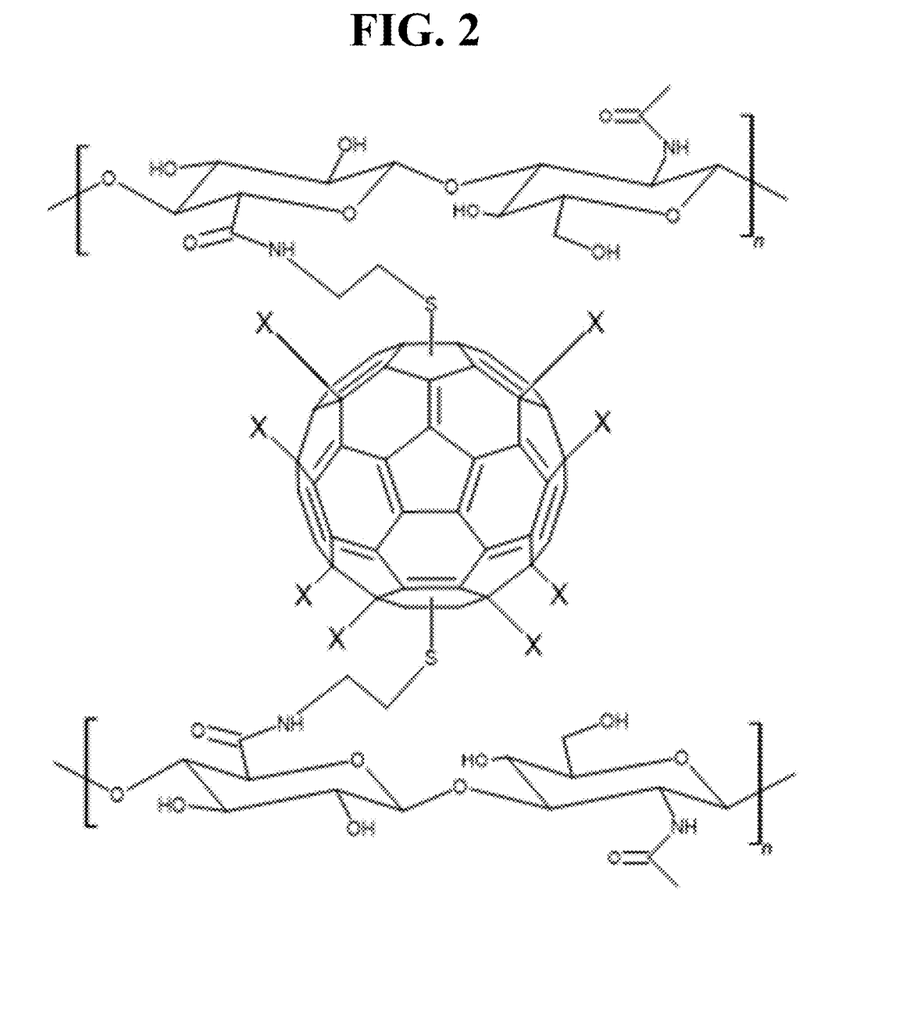
FIG. 2 is a molecular representation of an exemplary functionalized endohedral halo-fullerene of 60 carbons functionalized with halogens (X) and thiolated hyaluronic acid attached to the fullerene cage.

In a second embodiment of the present innovation, the ophthalmic solution formulation may encompass halo-fullerenes modified with thiolated Hyaluronic Acid (HA) through thiol-ene click chemistry (FIG. 2). HA, a naturally occurring component in tears, possesses distinctive moisture-retention properties, and serves as an eye lubricant. Including linkers can be advantageous to functionalization as they provide greater flexibility in terms of the distance between the bulk structure of HA and the fullerene cage. This modification optimizes ocular delivery of halo-fullerenes, ensuring specific, effective interaction with ocular cells and tissues for enhanced therapeutic outcomes.

Figure 3:
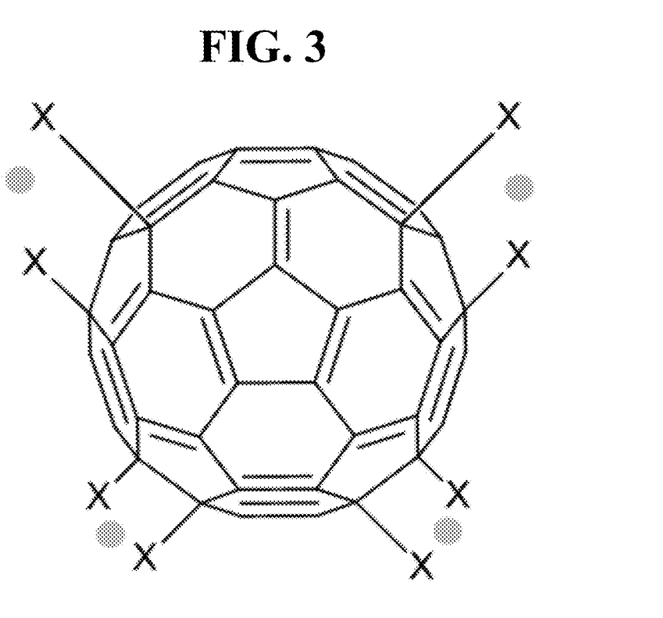
FIG. 3 is a molecular representation of an exemplary functionalized endohedral halo-fullerene of 60 carbons functionalized with halogens (X) and containing NPs (gray circle) attached to the fullerene cage.

A third embodiment of halo-fullerene may comprise the three typical functionalization patterns including: $C_{60}X_6$, $C_{60}X_8$ (FIG. 1), and $C_{60}X_{24}$; whereby X=a halogen molecule (e.g., iodine, bromine, chlorine or fluorine); whereas the composition may also comprise halo-fullerenes further modified with antimicrobial NPs (FIG. 3) on the exterior of the cage structure, such as metallic NPs (e.g., AgNPs). The halo-fullerene possesses an inherent molecular affinity for pathogenic species, augmented by the introduction of broad-spectrum antimicrobial halogens capable of prolonged microbial neutralization.

Figure 4:
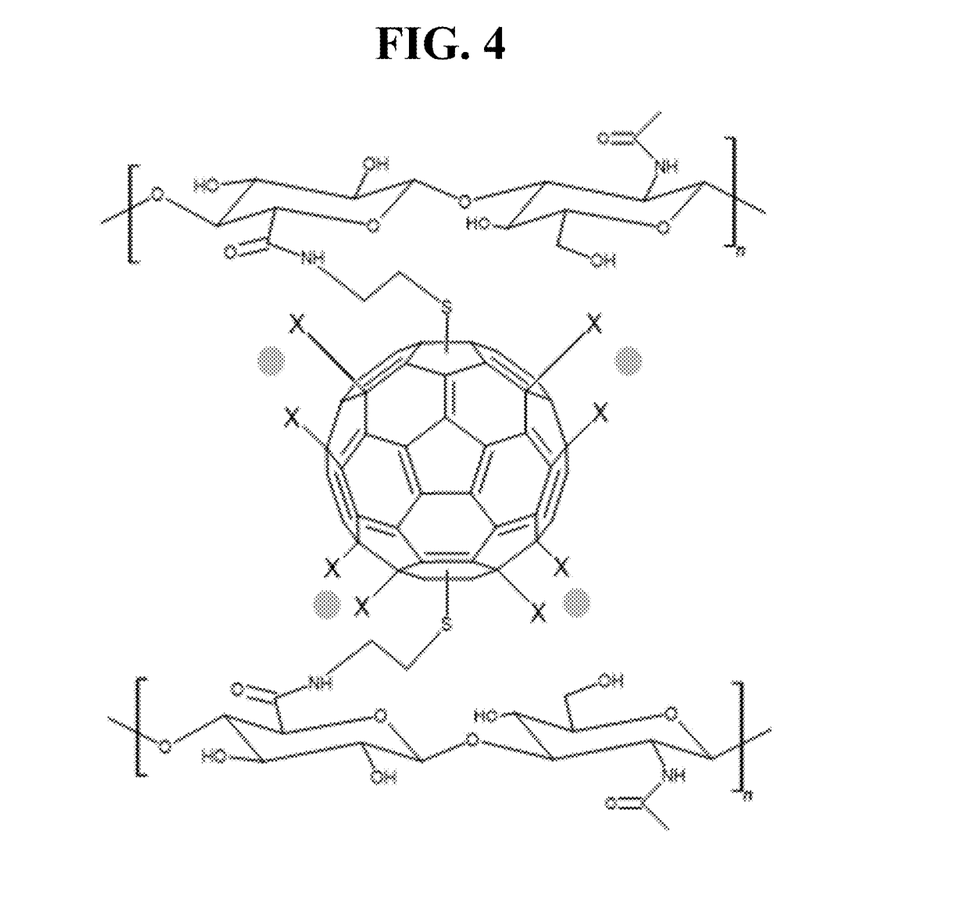
FIG. 4 is a molecular representation of an exemplary functionalized halo-fullerene of 60 carbons functionalized with halogens (X) and thiolated hyaluronic acid, containing NPs (gray circle) attached to the fullerene cage.
Figure 5:
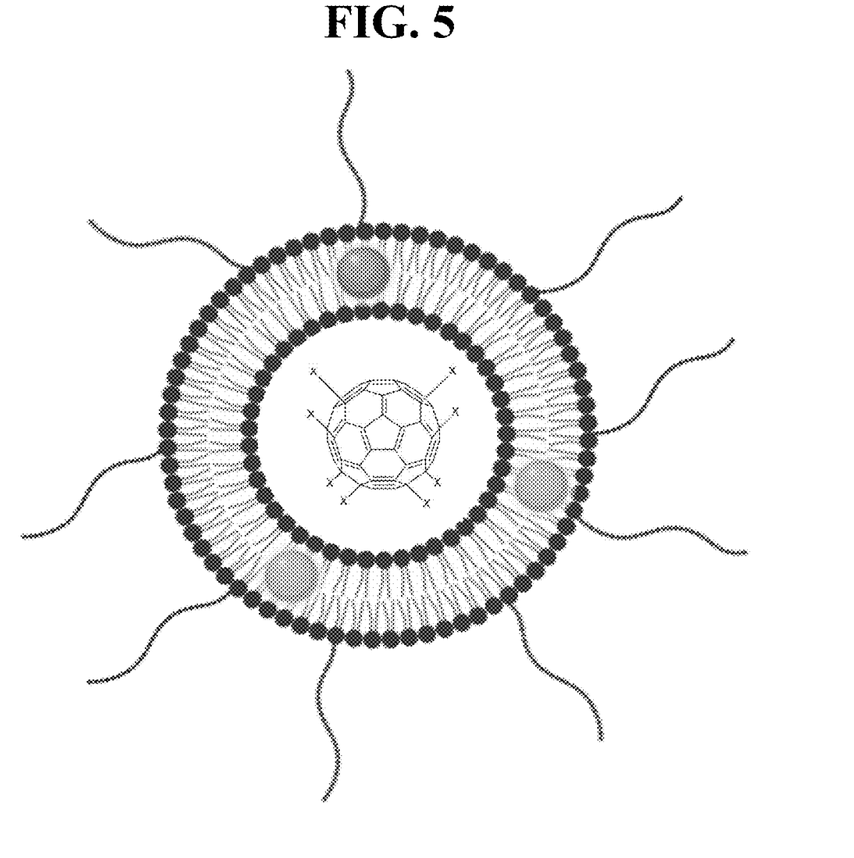
FIG. 5 is a molecular representation of an exemplary hyaluronic acid-modified liposomal encapsulated functionalized halo-fullerene of 60 carbons functionalized with halogens (X) attached to the fullerene cage and a liposomal bilayer containing NPs (grey).

In a fourth embodiment of the present invention, the composition may comprise a thiolated hyaluronic acid functionalized halo-fullerene with antimicrobial NPs on the exterior of the cage structure (FIG. 4). In another aspect of the present invention, the composition may comprise a combination of the halo-fullerene and silver nanoparticles loaded inside liposomal hyaluronic acid (FIG. 5).

Figure 6:
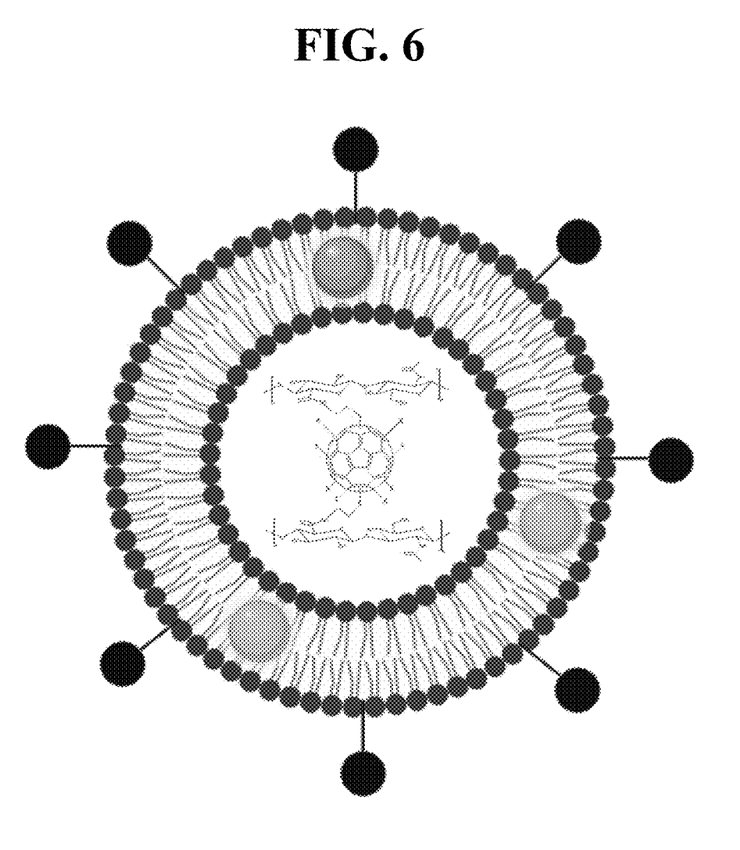
FIG. 6 is CSA molecular representation of an exemplary inclusion of Cyclosporin A-modified liposomal encapsulated functionalized halo-fullerene of 60 carbons functionalized with halogens (X) attached to the fullerene cage and a liposomal bilayer containing NPs (grey).

In another aspect of the present invention, the formulation may encompass an optional pharmacologically active ingredient, such as Cyclosporine A, which is attached to the liposomal surface by cyclosporine-phospholipid conjugates. Herein, the liposome structure comprises halo-fullerenes that have been subject to modification through thiolated hyaluronic acid (HA) incorporation within the core, accompanied by the presence of antimicrobial metallic nanoparticles (e.g., AgNPs) within the bilayer (FIG. 6).

In this embodiment, Cyclosporine A can be delivered onto the liposomal surface to extend the longevity of ocular cells, thereby yielding enhanced interstitial benefits. The synergistic action of Cyclosporine A with the liposomal structure results in a dual-pronged approach, characterized by surface-level and interstitial antimicrobial activity to block radiation and ocular toxin exposure. These features play a crucial role in preserving appropriate moisture levels throughout major cellular processes, which promotes cellular integrity in the mitigation of CDE.

In other embodiments, the combination of the halo-fullerene antimicrobial activity, antioxidative protection and molecular lubrication would complement ophthalmic solutions used in the cleaning, wetting and storage of soft and rigid gas-permeable contact lenses, without the need for antibiotic additives or preservatives. Such applications would be obvious to those skilled in the art for this segment.

The compositions of the present invention may further comprise pharmaceutically acceptable buffering agents to enhance stability and longevity including but not limited to: acetate, borate and phosphate buffers at concentrations in the ranges of 0.1% to 2.5% for the ophthalmic solution. These agents regulate and maintain the pH within the desired range of 6.0 to 8.0 of the suspension.

The incorporation of nutritive agents can leverage the extended life cycle of ocular cells, providing enhanced interstitial advantages for all embodiments. These may include but not be limited to: Vitamin A, which promotes corneal membrane health; Vitamin C, a protective antioxidant that bolsters collagen production; Vitamin E, a fat-soluble antioxidant; glutathione (antioxidant); Omega3 FAs that boost the lipid layer of the tear film; Zinc, which has also been shown to lower macular degeneration risk; and Lutein and zeaxanthin, which have been shown to provide UV protection. As these nutritive agents bolster cellular growth and vitality, the halo-fullerenes exhibit a dual-action approach that combines surface and interstitial antimicrobial activity while mitigating exposure to ocular toxins and radiation. These properties are instrumental in maintaining optimal moisture levels throughout cellular processes, resulting in a visibly smoother ocular surface through the promotion of cellular integrity.

What is claimed:

1. An ophthalmic solution composition for prevention and treatment of chronic dry eye and other ocular maladies comprising:
   a. thiolated hyaluronic acid functionalized endohedral halo-fullerenes of $C_{2n}X$, wherein n ranges from 10 to 360, and the halo-fullerenes have multiple side-chains of halogens attached to a carbon cage, and wherein said halo-fullerenes possess functionalization patterns selected from the group consisting of $C_{60}X_6$, $C_{60}X_8$, and $C_{60}X_{24}$, wherein X is a halogen molecule selected from the group consisting of iodine, bromine, chlorine, and fluorine;

b. an aqueous delivery vehicle;
c. a penetration enhancer;
d. optionally a pharmacologically active ingredient;
wherein said thiolated hyaluronic acid functionalized endohedral halo-fullerenes are modified via thiol-ene click chemistry and provide antimicrobial activity, antioxidative protection, molecular lubrication, and shielding from external irritants, facilitating penetration through ocular barriers without the need for antibiotic additives or preservatives.

2. The ophthalmic solution composition of claim 1, wherein the halo-fullerenes are enriched with silver nanoparticles.

3. The ophthalmic solution composition of claim 1, wherein the thiolated hyaluronic acid functionalized endohedral halo-fullerenes provide enhanced moisture-retention properties and serve as an eye lubricant.

4. The ophthalmic solution composition of claim 1, wherein the halo-fullerenes further comprise antimicrobial nanoparticles on the exterior of the carbon cage.

5. The ophthalmic solution composition of claim 4, wherein the antimicrobial nanoparticles are silver nanoparticles.

6. The ophthalmic solution composition of claim 5, wherein said halo-fullerenes and silver nanoparticles are encapsulated liposomal hyaluronic acid.

7. The ophthalmic solution composition of claim 1, further comprising pharmaceutically acceptable buffering agents that maintain a pH within a range of 6.0 to 8.0.

8. The ophthalmic solution composition of claim 1, wherein the halo-fullerenes disrupt the hydrogen-bonding network of water molecules at the surface, reducing surface tension and enhancing the spread and penetration of the composition on applied surfaces.

9. The ophthalmic solution composition of claim 1, wherein the halo-fullerenes maintain tear functions, improve tear film uniformity, and stabilize tear osmolarity.

10. The ophthalmic solution composition of claim 1, wherein the penetration enhancer facilitates increased absorption of the halo-fullerenes and the optional pharmacologically active ingredient(s) through the cornea and conjunctiva.

11. The ophthalmic solution composition of claim 1, wherein the halo-fullerenes provide sustained activity against pathogens and oxidative stress, consistent with extended cellular turnover cycles.

12. The ophthalmic solution composition of claim 1, wherein the composition is free from preservatives.

13. The ophthalmic solution composition of claim 1, wherein the halo-fullerenes act as a free-radical scavenger to minimize oxidative damage to ocular tissues.

14. The ophthalmic solution composition of claim 1, wherein the halo-fullerenes demonstrate consistent antimicrobial properties to maintain sterility, without the addition of caustic preservatives or secondary biocidal agents.

15. The ophthalmic solution composition of claim 1, wherein the halo-fullerenes can enhance the bioavailability of ophthalmic compounds when incorporated into the composition.

16. The ophthalmic solution composition of claim 1, wherein the penetration enhancer is selected from the group consisting of cyclodextrins, surfactants, and polymeric micelles.

17. The ophthalmic solution composition of claim 1, wherein said composition is compatible with contact lens use, ensuring lens clarity free of protein deposits.

18. The ophthalmic solution composition of claim 1, wherein said composition aids in the repair of epithelial defects and promotes healing of an ocular surface post-injury.

* * * * *